(12) United States Patent
Goetz

(10) Patent No.: US 6,314,384 B1
(45) Date of Patent: Nov. 6, 2001

(54) MEDICATION MANAGEMENT APPARATUS

(76) Inventor: Gerald E. Goetz, 15304 Sisson Rd., Penn Valley, CA (US) 95946-9535

( * ) Notice: Subject to any disclaimer, the term of this patent is extended or adjusted under 35 U.S.C. 154(b) by 0 days.

(21) Appl. No.: 09/261,044

(22) Filed: Mar. 2, 1999

Related U.S. Application Data

(60) Provisional application No. 60/076,943, filed on Mar. 4, 1998.

(51) Int. Cl.[7] ............................... G04F 10/00; G04F 8/00
(52) U.S. Cl. ......................... 702/177; 702/176; 368/109; 368/111
(58) Field of Search .................................... 702/176, 177, 702/178; 368/10, 107–111; 705/2, 3; 706/902, 923–924

(56) References Cited

U.S. PATENT DOCUMENTS

| | | | |
|---|---|---|---|
| 4,926,572 | 5/1990 | Holmes | 40/448 |
| 4,970,669 | 11/1990 | McIntosh et al. | 364/569 |
| 5,157,640 | 10/1992 | Backner | 368/10 |
| 5,239,491 | 8/1993 | Mucciacciaro | 364/569 |
| 5,289,157 | * 2/1994 | Rudick et al. | 368/109 |
| 5,408,443 | 4/1995 | Weinberger | 368/10 |
| 5,602,802 | * 2/1997 | Leigh-Spencer et al. | 368/10 |
| 5,852,590 | * 12/1998 | De la Huerga | 368/10 |
| 5,924,074 | * 7/1999 | Evans | 705/3 |
| 6,081,786 | * 6/2000 | Barry et al. | 705/3 |

OTHER PUBLICATIONS

Medi Track Advertisement, Jul. 2, 1992 issue of *U.S. News & World Report* (1 Page).

* cited by examiner

Primary Examiner—Marc S. Hoff
Assistant Examiner—Bryan Bui
(74) Attorney, Agent, or Firm—John R. Wahl; Merchant & Gould

(57) ABSTRACT

A portable system for reminding a patient and keeping track of the prescription and use of medications. The system comprises a portable unit and a software application program loaded in a PC-type computer. The portable unit consists mainly of a compact portable housing which contains an LCD display; audible alerts; pushbutton controls; battery power; and electronic circuitry to receive, store and display data. The portable unit can be programmed with dosage information regarding the particular medication, track when a particular medication has been taken, and sound an alarm when time to take another dose. The portable unit also checks for contraindications and warns of adverse reactions the patient would have with a particular drug or if a particular drug cannot be mixed with another drug presently being taken by the patient. The portable unit can receive, store, and display a patient's medical history, which can be downloaded from a PC-type computer loaded with the software application program that allows the computer to receive, store and download information regarding a patient's medical history and contraindication table. An enhancement is possible for the blind such that an audible voice informs the patient to take a particular pill number.

14 Claims, 6 Drawing Sheets

MEDICATION MANAGEMENT APPARATUS

CROSS-REFERENCE TO RELATED APPLICATIONS

This application claims the benefit of the filing date of U.S. Provisional Patent Application Ser. No. 60/076,943, filed Mar. 4, 1998.

BACKGROUND OF THE INVENTION

1. Field of the Invention

This invention pertains generally to devices for reminding a person when to take medication, and more particularly to a medication management system for tracking a patient's medication administration schedule, reminding the patient to take medication, and warning the patient of contraindications between multiple medications.

2. Description of the Related Art

When medication is prescribed, a patient often fails to adhere to the administration and dosage instructions specified for the medication. As a result of busy schedules and other distractions, it is not difficult for a patient to forget the specific time that the medication is to be taken or simply lose track of time and forget to take the medication. The patient may either skips a dose altogether or take a dosage outside of the prescribed time interval. This can lead to a variety of pharmacological and/or toxicological problems to the patient which, ultimately, may result in ineffective treatment of a disease and/or harm to the patient.

In addition, patients who are required to take several different medications during the course of a day may become confused with the frequency and particular medication that needs to be taken at a particular time, also resulting in the above-stated problems. These problems may be exacerbated when the patient is busy, has a failing memory, impaired vision, or is incoherent due to the illness or effects of the medication. Many patients carry written "timetables" with them, often with actual pills taped to then, to help them take their medications. If they should forget to look at the timetable, however, it would result in the patient missing one or more medications.

Another, and very serious problem, with multiple medications taken by a patient is the possibility of adverse effects, or contraindications, among medications that are taken together or at improper intervals. It is possible that contraindications could be overlooked, particularly if a patient has multiple health care providers and forgets to give each health care provider complete information about other prescribed medications.

There are devices which provide various means for alerting a patient when and what medication should be taken. However, none of the devices allow input and storage of a patient's medication information, contraindication tables, use times and medical history information, and the display and annunciation of use times and medical contraindications.

Therefore, a need exists for a portable medication storage and reminder apparatus with the capability for the input of a patient's medication information, contraindication tables, use times and medical history information; and for the display and annunciation of use times and medical contraindication. The present invention satisfies those needs, as well as others, and overcomes the deficiencies found in prior technology.

SUMMARY OF THE INVENTION

The present invention pertains to a medication management system generally comprising a portable programmable table unit which tracks a patient's medication administration schedule, reminds the patient to take medication, and warns the patient of contraindications between multiple medications, and provides a download station for inputting, storing, editing and downloading the patient's medical history data, medication administration schedule, and contraindication table data to the portable unit.

By way of example, and not of limitation, the portable unit comprises a housing, a microprocessor/micro-controller unit with associated electronic circuitry, data storage capability, a pushbutton keypad, a visual display, an audible alert and a port for interfacing with a computer. The associated download computer includes a software program that allows a patient's medication, contraindication table, use times and medical history information to be inputted, edited, stored, and downloaded into the portable unit.

The portable unit can be programmed with medication dosage information, track when a particular medication has been taken, sound an alert when time to take another dosage, and warn of contraindications. The portable unit also has the capability to store and display a patient's medical history. The portable unit allows the patient's medication information, contraindication table, use times and medical history information to be downloaded from the central computer and stored within resident memory of the portable unit. The portable unit will annunciate the use time for a particular medication, and warn of contraindications that may result if medications are taken at other than the prescribed times. In addition, the portable unit allows the patient to change medication times, track when medication was taken and review the patient's data. An enhancement is available for the blind such that an audible voice informs the patient to take a particular pill number. The housing for the portable unit has a size and shape consistent in design for those who have challenged physical and visual capabilities.

An object of the invention is to provide a system which reminds a patient when it is time to take a medication.

Another object of the invention is to provide a system which will warn of contraindication existing within the patient's prescribed medications.

Another object of the invention is to provide a system which can receive and store a patient's medical history.

Another object of the invention is to provide a medication reminder system having a portable unit with the capability to interface with a computer system.

Yet another object of the invention is to provide a medication reminder system having a portable unit with an easily readable display while offering the patient a simplistic method of reminding when and which medication to take.

Further objects and advantages of the invention will be brought out in the following portions of the specification, wherein the detailed description is for the purpose of fully disclosing preferred embodiments of the invention without placing limitations thereon.

BRIEF DESCRIPTION OF THE DRAWINGS

The invention will be more fully understood by reference to the following drawings which are for illustrative purposes only.

DETAILED DESCRIPTION OF THE INVENTION

Referring more specifically to the drawings, for illustrative purposes the present invention is embodied in the apparatus and method generally shown in FIG. 1 through FIG. 7. It will be appreciated that the apparatus may vary as to configuration and as to details of the parts without departing from the basic concepts as disclosed herein.

Figure 1:
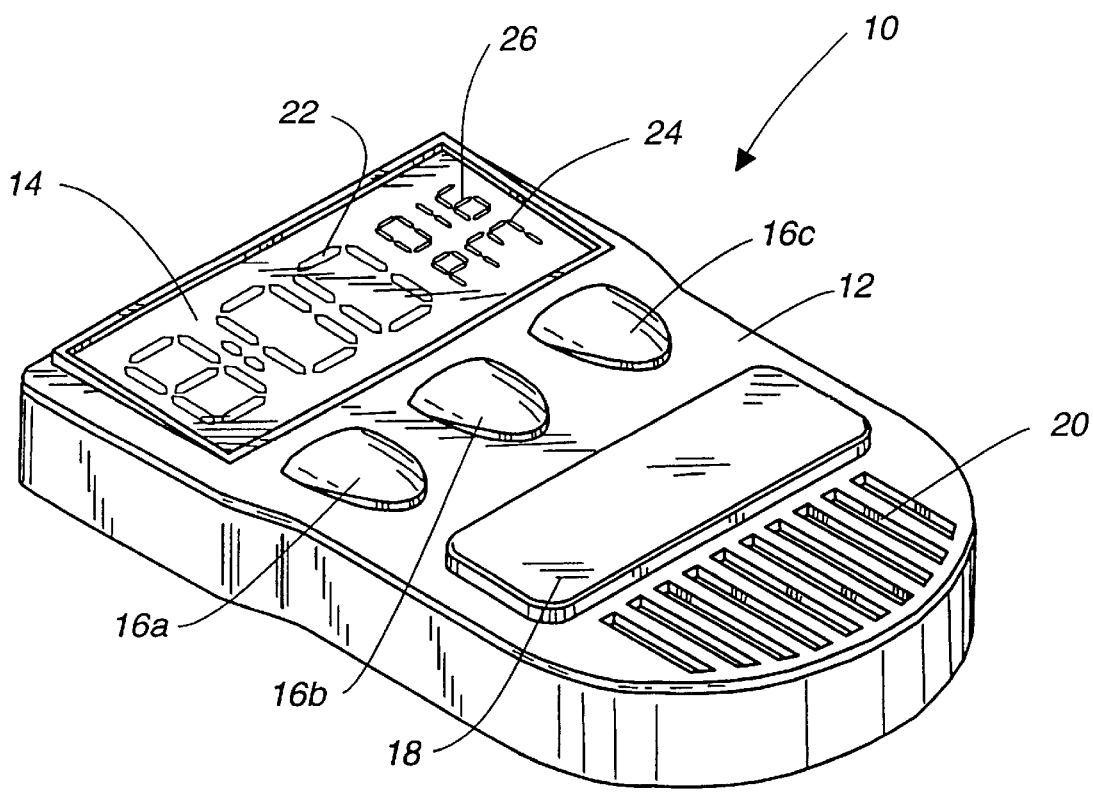
FIG. 1 is a perspective view of a portable computerized medication reminder unit in accordance with the present invention.

Referring first to FIG. 1, a preferred embodiment of the portable unit 10 is generally shown. The portable unit 1comprises a housing 12 constructed from a high-performance thermoplastic or similar material, a digital display 14, application function pushbuttons 16a, b, c, and main pushbutton 18. An audio annunciator 20 is located behind the front panel of housing 12 to allow for audible alarm indications.

In the preferred embodiment, digital display 14 is a 2 to 4 line by 16 character liquid crystal display (LCD) capable of being easily read even by the visually impaired. Alternatively a light emitting diode (LED), dot matrix or other display with alphanumeric capability could be used. Display 14 is scrollable, and is capable of displaying various alphanumeric data and user prompts, the patient's daily medication plan and an abbreviated version of the patient's medical history. In addition, digital display 14 displays a real-time clock 22 with AM or PM indicators 24. Along with clock display 22, the current "on deck" medication acronym 26 is also displayed. The acronym could be a graphical icon, numbers, letter and number combinations, or the like, which corresponds to a medication to be taken by the patient. For example, if a medication was identified as Ml, a matching sticker could be placed on the pill bottle or other medication container. At the proper time, the "on deck" medication acronym will blink indicating it is time to take that particular medication.

Application buttons 16 are arranged in such a fashion that they correlate with digital display 14 and some of the display functions. For example, a question may be prompted as to whether or not to change medication times; e.g., "Change medication time? Yes or No?". The section of digital display 14 closest to the corresponding application button 16 would indicate the particular function of application button 16; e.g., "Yes" or "No". The primary functions that are controlled by application buttons 16 are as follows: (a) Taking Medication Earlier or Later than Scheduled; (b) Editing Medication Times and (c) Reviewing Patient Data.

Audio annunciator 20, which can be an electronic bell, siren, buzzer, or other appropriate annunciating device, signals the user to indicate that it is time to take that particular medication. Annunciator 20 can also emit an audible signal to acknowledge when associated application button 16 entries are made if desired. Portable unit 10 optionally includes a magnetic strip (not shown) on the back to allow for mounting on a refrigerator or other appropriate ferrous surface. In the preferred embodiment of the invention, administration schedules for up to eight medications may be programmed into portable unit 10, and portable unit 10 will warn the patient of three of the medications that may be contraindicated.

Figure 2:
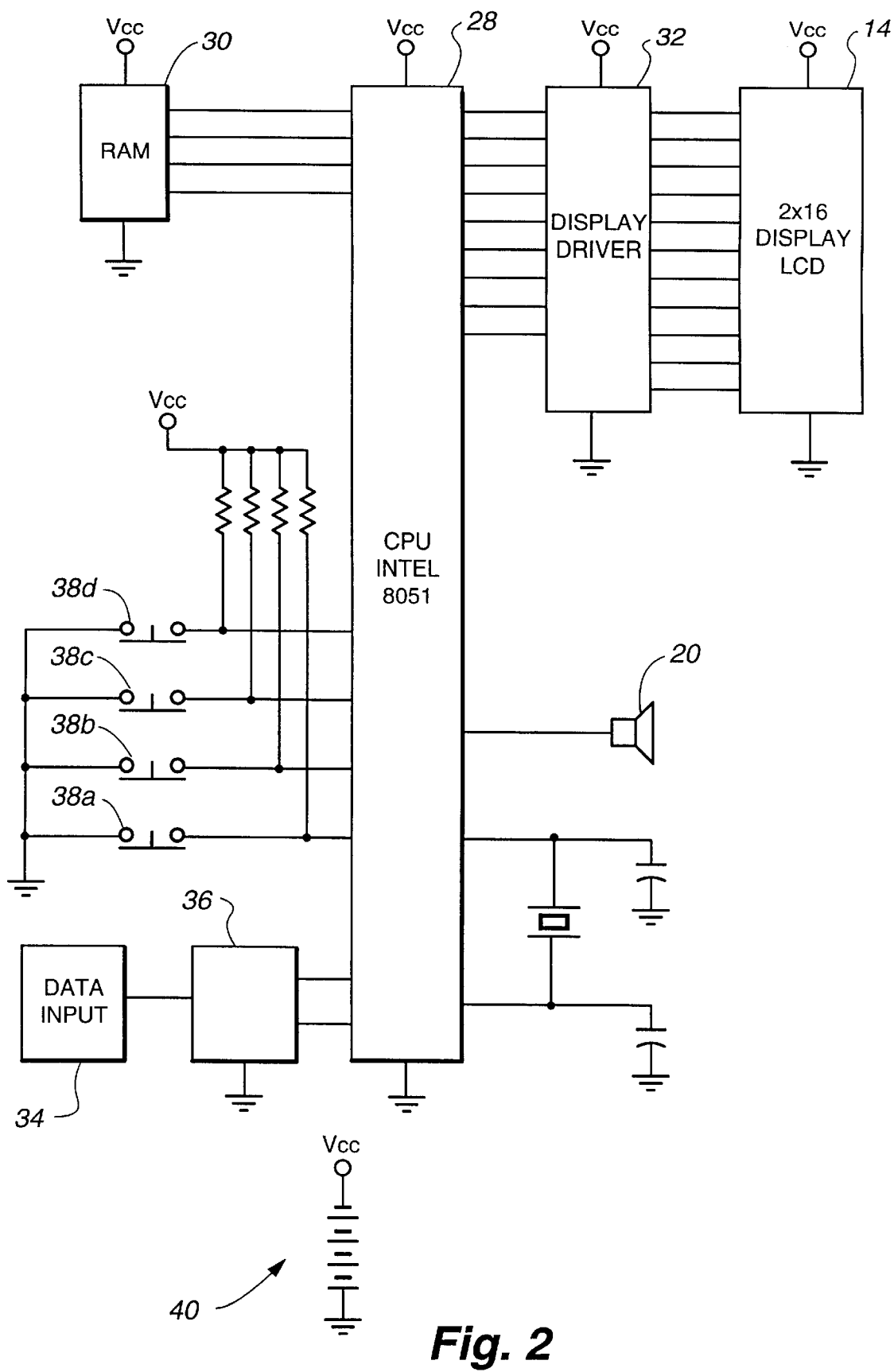
FIG. 2 is a functional block diagram of an embodiment of circuitry employed in the portable computerized medication reminder unit shown in FIG. 1.

Referring also to FIG. 2, portable unit 10 is preferably controlled by an 8-bit INTEL® 8051 microprocessor 28 or the like, although those skilled in the art will appreciate that other control processor means, such as analogous circuitry in either analog or digital form, may alternatively be used with portable unit 10. Data is stored in and retrieved from random access memory (RAM) 30, which is operatively coupled to microprocessor 28.

A display driver 32 is operatively coupled to microprocessor 28, and digital display 14 is operatively coupled to display driver 32. Data from an external source, such as a personal computer or the like (not shown), is downloaded to portable unit 10 via a data input port 34, which is also operatively coupled to microprocessor 28. Data input port 34 can be a serial interface connector which allows for the attachment of a standard cable, or an infrared, radio frequency or other communication input port through which the patient's medical data and contraindication table data can be transferred from the download computer. It is also contemplated that the communications interface could be bidirectional. A conventional communications interface 36 is provided as required. Four switches 38a, b, c, d, are operatively connected to application buttons 16a, b, c and main button 18, respectively, to provide input signals to microprocessor 28. Portable unit 10 is powered by a battery 40 with the option of using rechargeable batteries.

Figure 3:
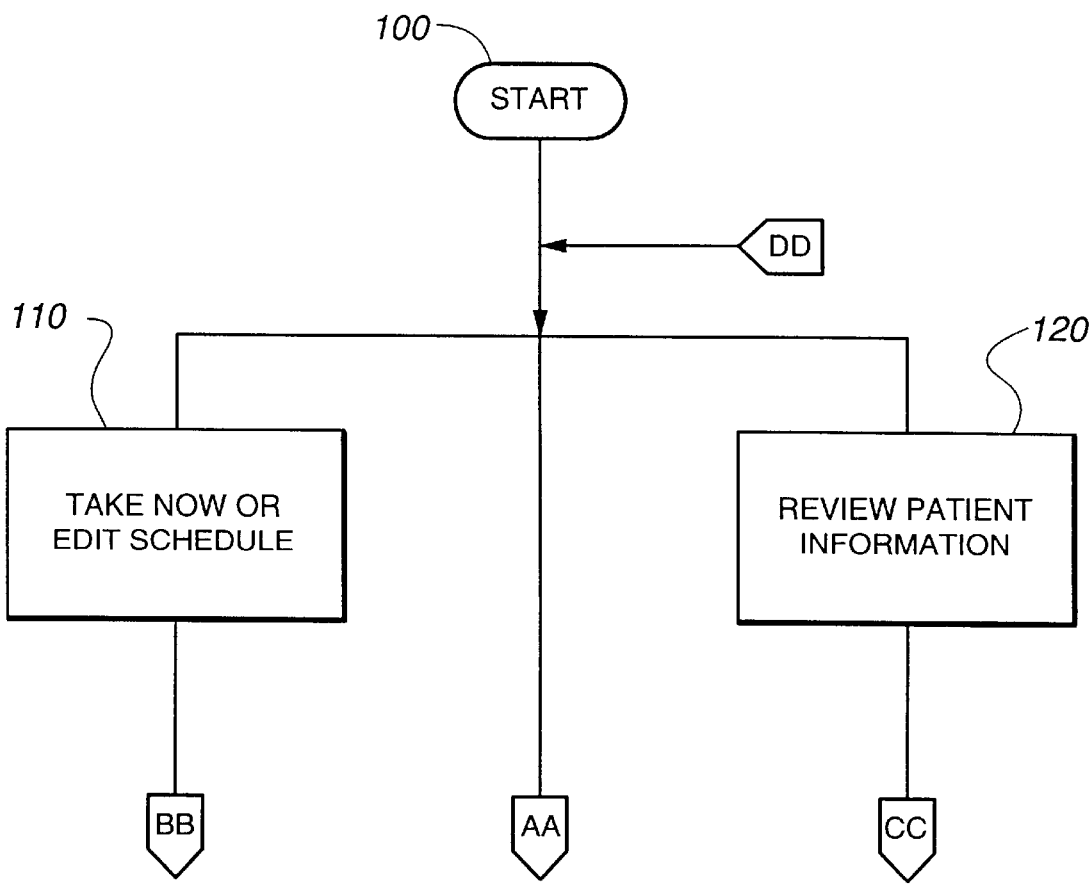
FIG. 3 through FIG. 6 are flow charts illustrating the operational sequence of the portable unit shown in FIG. 1.
Figure 4:
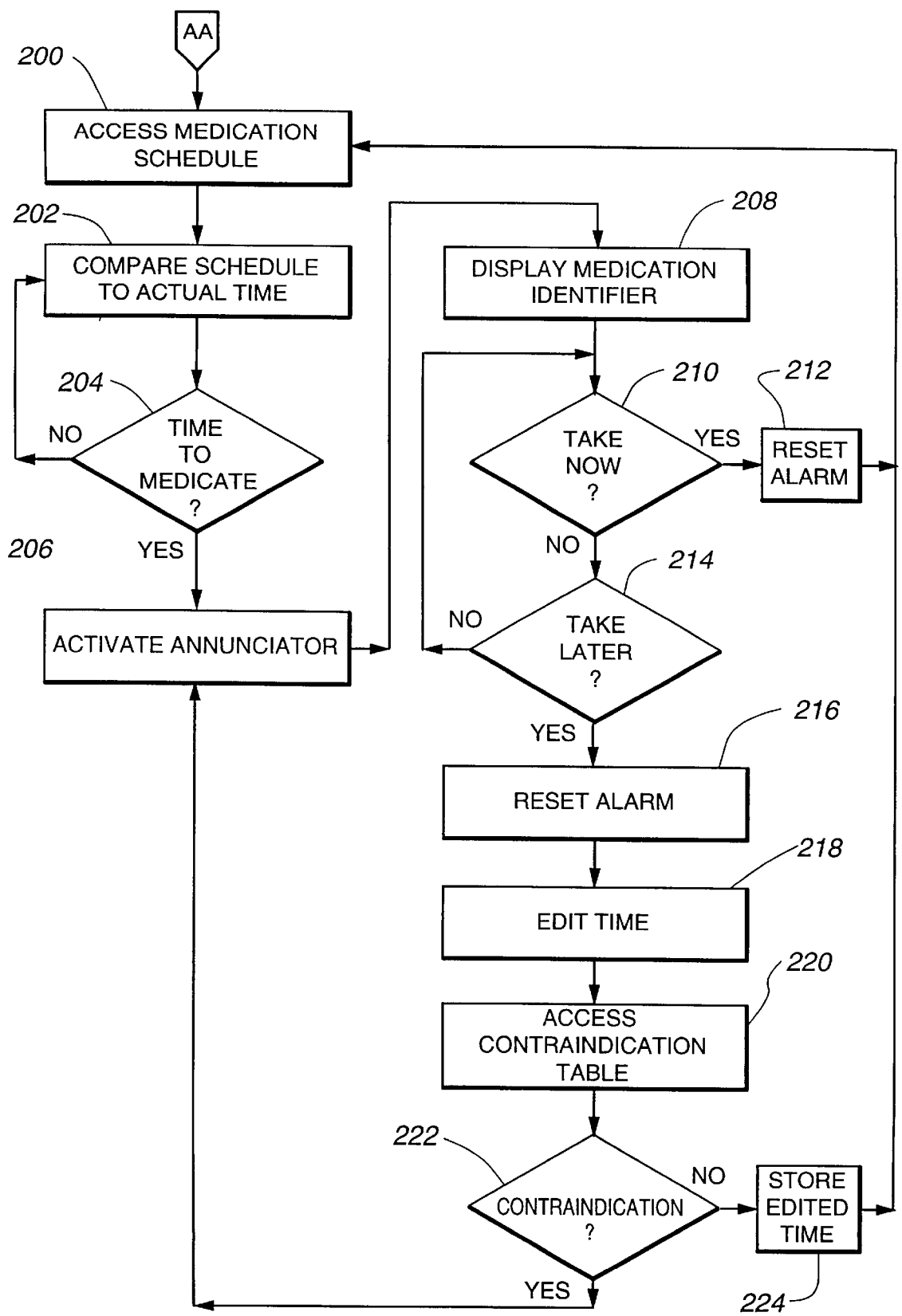
Figure 5:
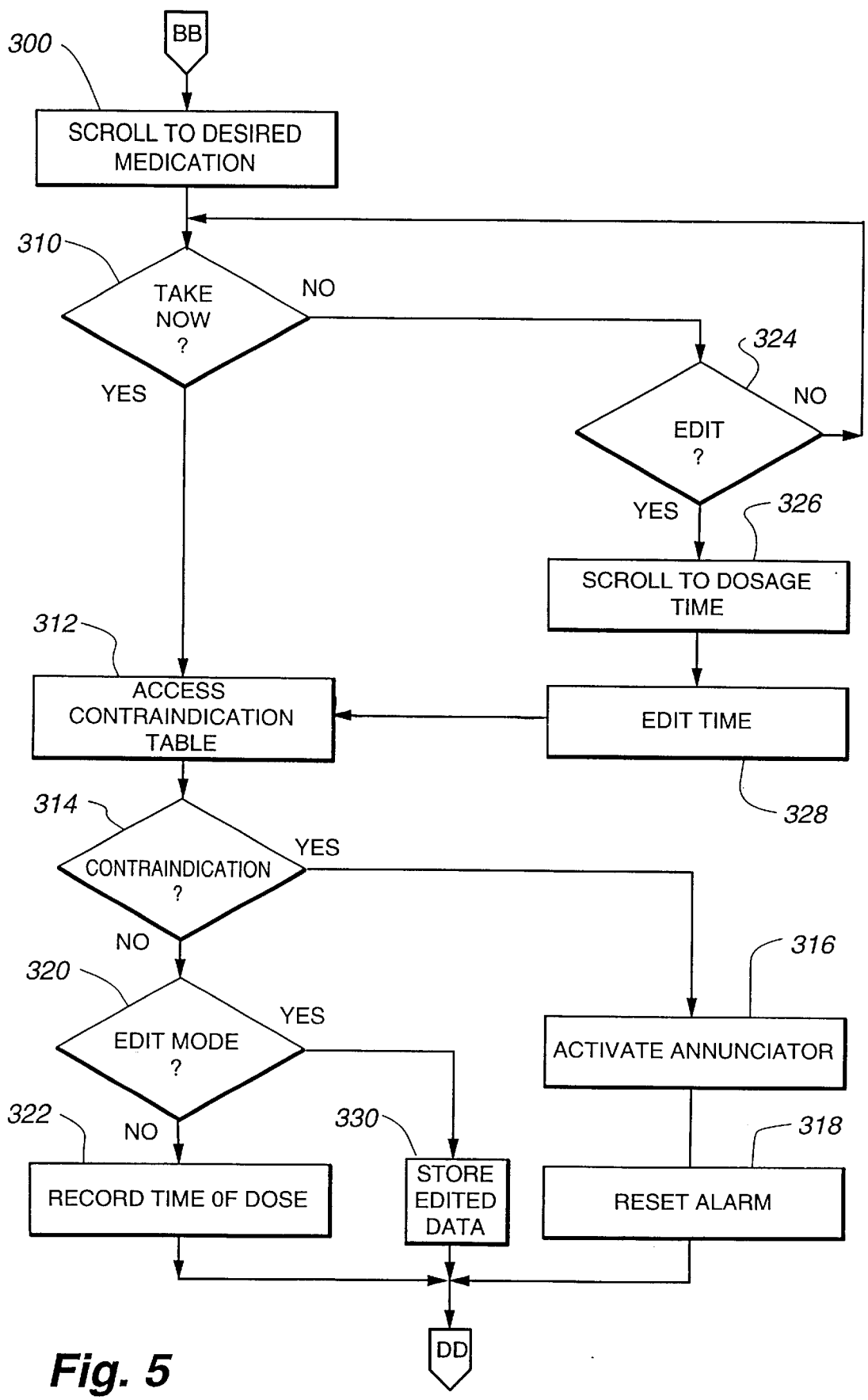

Referring also to FIG. 3 through FIG. 5, portable unit 10 employs software as outlined therein for implementing its primary functions. The software is encoded in microprocessor 28 using programming techniques which are conventional in the art. Referring first to FIG. 3, the program begins at step 100 on power-up or other activation. As can be seen, at this point the program invokes the subroutine shown in FIG. 4 for tracking the administration of the patient's medication. The user also has the opportunity to manually select one of the ancillary functions of the apparatus. For example, if the user desires to take a particular medication now or edit the medication schedule, he or she would select the application button corresponding to step 110. From there, the program would access a subroutine at step 300 (FIG. 5). If the user desires to review patient information, such as patient history, medical information such as medication allergies, or the like, he or she would select the application button corresponding to step 120 and the program would access a subroutine at step 400.

Referring now to FIG. 4, at step 200 the program accesses the medication schedule stored in RAM 30. At step 202, the scheduled times for medications to be administered are compared against the internal real-time clock in microprocessor 28. At step 204, a determination is made as to whether it is time to administer medication. If it is, at step 206 annunciator 20 is activated. Then, at step 208, the medication identifier or acronym 26 is displayed to inform the user of the particular medication to administer. At step 210, the user is then prompted for whether or not he or she wants to take the medication at that moment. If the user selects "Yes", the alarm is reset at step 212 and the user takes the medication. The routine then returns to step 200.

If the patient does not want to take the medication at that time, the user selects "No" at the prompt and the program proceeds to step 214 where the user is prompted for whether or not he or she wishes to take the medication later. If the user selects "No", the program returns to step 210 where the user is again prompted for whether or not he or she wants to take the medication now. If the user selects "Yes" to the prompt, the alarm is reset at step 216. At step 218, the user then edits the schedule for that particular medication, entering the new dosage time. The contraindication table is then accessed at step 220. At step 222, the program compares the new dosage time with data in the contraindication table and tests for a contraindication. If a contraindication exists, the program jumps to step 206 where the annunciator is once again activated to tell the user that the change is unacceptable and to give the user the opportunity to take this medication at the current time. If no contraindication is indicated, the edited dosage schedule is recorded at step 224 and the routine returns to step 200.

Referring now to FIG. 3 and FIG. 5, if the user wishes to take a dosage of medication at the present time (e.g., earlier than scheduled and before an alarm is sounded) or if the user wishes to edit the dosage schedule for a particular medication to take it later than scheduled, he or she selects the corresponding application button at step 110 in FIG. 3. This action invokes the subroutine shown in FIG. 5. Next, at step 300, the user scrolls to the desired medication identifier on display 14 and selects that medication. At step 310, the user is prompted for whether he or she wishes to take the medication now. If the user selects "Yes", the contraindication table is then accessed at step 312. At step 314, the program compares the current time for taking the dosage with the data in the contraindication table and tests for a contraindication. If a contraindication exists, the program proceeds to step 316 where the annunciator is activated to tell the user that it is unacceptable to take the medication now. The user can then reset the alarm at step 318 and the subroutine exits. If no contraindication is indicated at step 314, then at step 320 the program checks to determine if the edit mode had been previously selected. If the program is not in the edit mode, then the dosage time is recorded at step 322, the contraindication table is updated, and the subroutine exits. The user can then take the medication.

Figure 6:
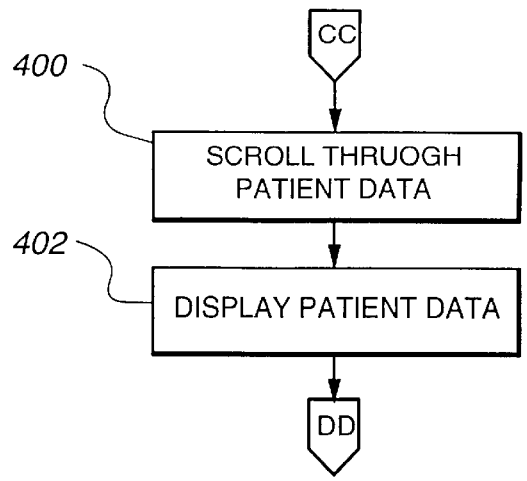

Otherwise, if at step 310 the user selects "No" in response to the "take now" prompt, the program proceeds to step 324 where the user is prompted to confirm that he or she wishes to edit the medication schedule. If the user selects "No", the program returns to step 310 to ask the user once again if he or she wishes to take the medication now. If the user selects "Yes" at step 324, then at step 326 the user is permitted to scroll to the dosage time to be edited. At step 328, the user then edits the schedule for that particular medication, entering the new dosage time. The contraindication table is then accessed at step 312. At step 314, the program compares the new dosage time with data in the contraindication table and tests for a contraindication. If a contraindication exists, the program proceeds to step 316 where the annunciator is activated to tell the user that the change is unacceptable. The user then resets the alarm at step 318 and the subroutine exits. If no contraindication is indicated at step 314, at step 320 the program checks to determine if it is in the edit mode and, if so, the edited data stored at step 330, the contraindication table is updated, and the subroutine exits. Referring to FIG. 3 and FIG. 6, if the user simply desires to review the medication administration schedule, patient history information or other stored information without making any changes, then the corresponding application button is pressed at step 120 in FIG. 3. This action then invokes the subroutine shown in FIG. 6 where, at step 400 the user can scroll through the data and the data is displayed at step 402. It will be appreciated that the software could easily include the capability of editing the medication administration schedule from this review mode if desired.

In general terms, the contraindication simulation is applied to three medications. Two of the medications will be warned (annunciated by alarm on the portable unit 10) if taken together (in the same time frame of 1 hour).

One medication will be warned if taken with aspirin or other over the counter medication.

Figure 7:
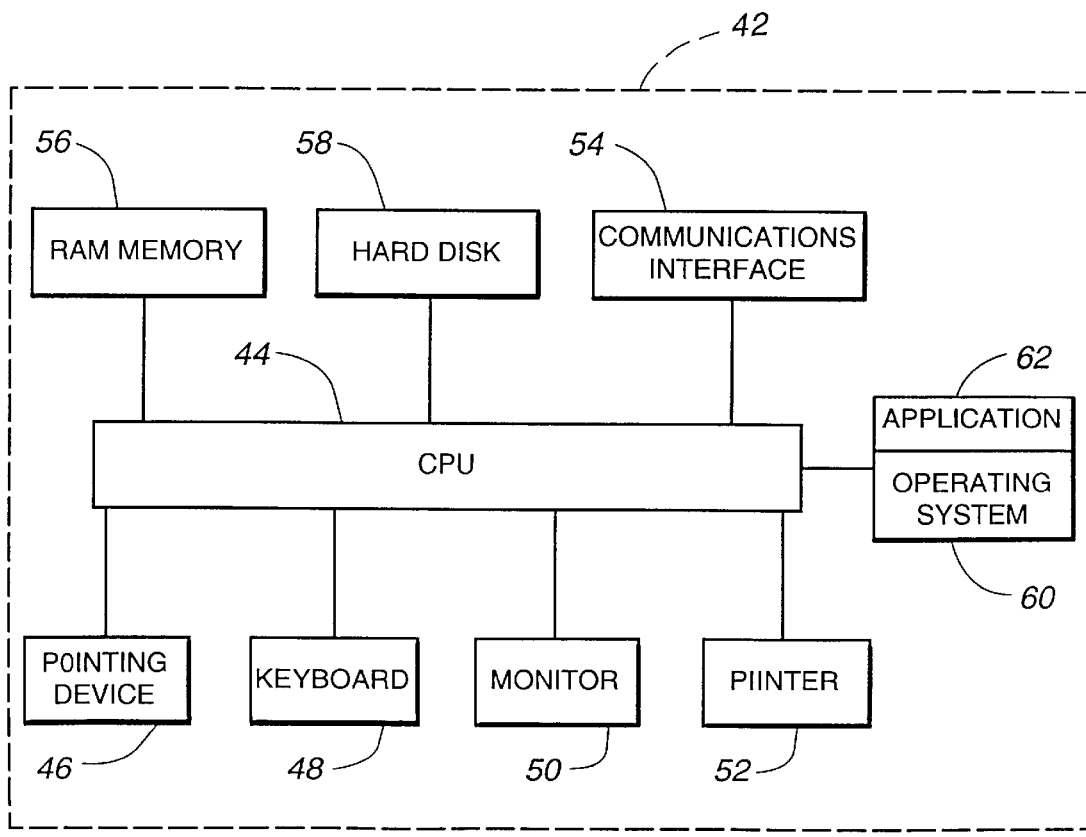
FIG. 7 is a functional block diagram of a download station in accordance with the present invention.

Referring now to FIG. 7, there is shown a functional block diagram of the download computer 42 used for inputting, editing, storing and transferring information about the patient to portable unit 10. The download computer can be a personal computer or the like of a known configuration which generally includes a central processing unit 44, pointing device (mouse) 46, keyboard 48, monitor 50, printer 52, communications interface 54, random access memory 56, disk storage 58, appropriate operating system software 60 for the platform, and MedicationMinder download application software 62.

The MedicationMinder software 62 is an application program written in Visual Basic™, or other appropriate developers language, that allows a system administrator, such as a physician or pharmacist, to input information, via keyboard, into the computer for storage and transfer to portable unit 10. Generally, the application program carries out the operations of:

(i) allowing a patient's medical history data and contraindication table data to be inputted by an operator using the computer's keyboard;

(ii) allowing a patient's medical history data and contraindication table data to be edited using the computer's keyboard;

(iii) storing a patient's medical history data and contraindication table data within data storage means; and (iv) downloading a patient's medical history data and contraindication table data to said portable unit.

The application program would typically prompt for information via a "form-on-screen" method. "TAB", "ENTER", or "ARROW" keys on the keyboard would allow the administrator to move from prompt to prompt on the above mentioned form-on-screen. Once the data has been inputted, it will then be saved to the hard disk 58. The administrator may also download the data into the portable unit 10 at this time through communications interface 54 by, for example, attaching a serial cable between download computer 42 and portable unit 10. The administrator would select, using the pointing device, tab or arrow keys, an appropriate file from the application program menu to download into portable unit 10. The administrator would then select a "DOWNLOAD" command from the program menu to begin the download operation.

The "form-on-screen" would typically prompt for the following items: First Name, Last Name, Middle Initial, Address 1 (Street or P.O. Box), Address 2 (City and State), Address 3 (Zip Code), Daytime Phone Number, Evening Phone Number, Phone Number of Friend in Case of Emergency, Date of Birth, Social Security Number (if desired), Name of Attending Physician, Phone Number of Attending Physician, Medication #1 and preferred times (up to 6 input times), Medication #2 and preferred times (up to 6 input times), Medication #3 and preferred times (up to 6 input times), Medication #4 and preferred times (up to 6 input times), Medication #5 and preferred times (up to 6 input times), Medication #6 and preferred times (up to 6 input times), Medication #7 and preferred times (up to 6 input times), Medication #8 and preferred times (up to 6 input times), Allergies (2 lines by 16 chars) and Current Medical History Summary (2 lines by 16 characters).

Once entered, the above information may be stored on hard disk 58 or printed on printer 52 as a hard copy record. The hard copy record may also be used as a approval process document for doctor, patient and pharmacist if required. Following approval of the data stored in memory, the administrator may choose to download the information into portable unit 10.

Those skilled in the art will appreciate that the software functions described above can be implemented using conventional programming techniques, and that the actual program code will vary from platform to platform. In addition, it will be appreciated that the program steps and their sequence can vary without departing from the present invention. Furthermore, those skilled in the art will appreciate that the hardware configuration and specific hardware elements employed can vary without departing from the present invention. For example, analog and digital equivalents could be used, and the functions described herein can be implemented with alternative circuit configurations. Although the description above contains many specificities, these should not be construed as limiting the scope of the invention but as merely providing illustrations of some of the presently preferred embodiments of this invention. Thus the scope of this invention should be determined by the appended claims and their legal equivalents.

What is claimed is:

1. A portable medication reminder and contraindication warning apparatus, comprising;
   (a) a housing; and
   (b) control processor means contained within said housing for storing a medication administration schedule, for storing a medication contraindication table, for activating a medication administration reminder signal responsible to said medication administration schedule, and for activating a medication contraindication warning signal responsible to said medication contraindication table and a change in said medication administration schedule caused by a user's delay in or omission of administering a dose of medication.

2. An apparatus as recited in claim 1, further comprising means for providing an audible medication administration reminder signal and an audible medication contraindication warning signal.

3. An apparatus as recited in claim 1, further comprising means for providing a visual medication administration reminder signal and a visual medication contraindication warning signal.

4. A portable medication reminder and warning apparatus, comprising:
   (a) a housing;
   (b) control processor means contained within said housing for storing a medication administration schedule, for editing said medication administration schedule, for storing a medication contraindication table, for activating a medication administration reminder signal, and for activating a medication contraindication warning signal caused by a user's delay in or omission of administering a dose of medication; and
   (c) data interface means for downloading said medication administration schedule and said contraindication table from an external download processor.

5. An apparatus as recited in claim 4, further comprising means for providing an audible medication administration reminder signal and an audible medication contraindication warning signal.

6. An apparatus as recited in claim 4, further comprising means for providing a visual medication administration reminder signal and a visual medication contraindication warning signal.

7. An apparatus is recited in claim 4, further comprising:
   (a) an external download processor; and
   (b) an application software program associated with said download processor, said application software program including means for:
      (i) inputting, editing and storing said medication contraindication table;
      (ii) inputting, editing and storing said medication administration schedule; and
      (iii) transferring said contraindication table and said medication administration table to said control processor means.

8. A portable medication reminder and contraindication warning apparatus, comprising:
   a housing; and
   control processor means contained within said housing for storing a medication administration schedule, for storing a medication contraindication table, for activating a medication administration reminder signal responsible to said medication administration schedule, and for activating a medication contraindication warning signal responsible to said medication contraindication table and a change in said medication administration schedule, wherein said control processor means includes software program means for:
   (a) determining from said medication administration schedule whether it is time for a dose of medication to be administered;
   (b) activating said medication administration reminder signal when it is time for said dose of medication to be administered;
   (c) when said medication administration reminder signal is activated, displaying an option of changing said medication administration schedule and taking said dose of medication at a later time;
   (d) testing for a contraindication if a user changes said medication administration schedule; and
   (e) activating said contraindication warning signal if a contraindication is found.

9. A portable medication reminder and warning apparatus, comprising:
   (a) a housing;
   (b) control processor means contained within said housing for storing a medication administration schedule, for editing said medication administration schedule and for storing a medication contraindication table;
   (c) data interface means for downloading said medication administration schedule and said medication contraindication table from an external download processor;
   (d) means for providing a medication administration reminder signal and activating a medication contraindication warning signal caused by a user's delay or omission of administering a dose of medication; and
   (e) data input means for acknowledging said medication administration signal and said medication contraindication warning signal.

10. A portable medication reminder and warning apparatus, comprising:
   a housing;
   control processor means contained within said housing for storing a medication administration schedule, for editing said medication administration schedule and for storing a medication contraindication table;
   data interface means for downloading said medication administration schedule and said medication contraindication table from an external download processor;
   means for providing a medication administration reminder signal and a medication contraindication warning signal; and data input means for acknowledging said medication administration signal and said medication contraindication warning signal;

wherein said control processor means includes software program means for:

(a) determining from said medication administration schedule whether it is time for a dose of medication to be administered;

(b) activating said medication administration reminder signal when it is time for said dose of medication to be administered;

(c) when said medication administration reminder signal is activated, displaying an option of changing said medication administration schedule and taking said dose of medication at a later time;

(d) testing for a contraindication if a user changes said medication administration schedule; and (e) activating said contraindication warning signal if a contraindication is found.

11. An apparatus is recited in claim 10, further comprising:

(a) an external download processor; and (b) an application software program associated with said download processor, said application software program including means for:

(i) inputting, editing and storing said contraindication table;

(ii) inputting, editing and storing said medication administration schedule; and (iii) transferring said contraindication table and said medication administration table to said control processor means.

12. A portable medication reminder and warning apparatus, comprising:

(a) a housing;

(b) control processor means contained within said housing for storing a medication administration schedule, for editing such medication administration schedule and for storing a medication contraindication table;

(c) data interface means for downloading said medication administration schedule and said contraindication table from an external download processor;

(d) means for providing an audible medication administration reminder signal and activating an audible medication contraindication warning signal caused by a user's delay or omission of administering a dose of medication;

(e) data input means for acknowledging said medication administration signal and said medication contraindication warning signal; and (f) means for visually displaying data associated with said medication administration schedule.

13. A portable medication reminder and warning apparatus, comprising:

a housing;

control processor means contained within said housing for storing a medication administration schedule, for editing such medication administration schedule and for storing a medication contraindication table;

data interface means for downloading said medication administration schedule and said contraindication table from an external download processor;

means for providing an audible medication administration reminder signal and an audible medication contraindication warning signal;

data input means for acknowledging said medication administration signal and said medication contraindication warning signal; and means for visually displaying data associated with said medication administration schedule, wherein said control processor means includes software program means for:

(a) determining from said medication administration schedule whether it is time for a dose of medication to be administered;

(b) activating said medication administration reminder signal when it is time for said dose of medication to be administered;

(c) when said medication administration reminder signal is activated, displaying an option of changing said medication administration schedule and taking said dose of medication at a later time;

(d) testing for a contraindication if a user changes said medication administration schedule; and (e) activating said contraindication warning signal if a contraindication is found.

14. An apparatus as recited in claim 13, further comprising:

(a) an external download processor; and (b) an application software program associated with said download processor, said application software program including means for:

(i) inputting, editing and storing said contraindication table;

(ii) inputting, editing and storing said medication administration schedule; and (iii) transferring said contraindication table and said medication administration table to said control processor means.

* * * * *